United States Patent
Holman et al.

(10) Patent No.: US 6,479,546 B1
(45) Date of Patent: Nov. 12, 2002

(54) ALLOSTERIC INHIBITORS OF LIPOXYGENASE

(75) Inventors: Theodore Russell Holman, Santa Cruz, CA (US); Rakesh Mogul, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/625,915

(22) Filed: Jul. 26, 2000

(51) Int. Cl.⁷ .............................................. A61K 31/195
(52) U.S. Cl. ....................................................... 514/562
(58) Field of Search ......................................... 514/562

(56) References Cited

U.S. PATENT DOCUMENTS

| | | | |
|---|---|---|---|
| 4,645,627 A | 2/1987 | van Paassen et al. | ... 260/501.21 |
| 5,037,992 A | 8/1991 | Ward et al. | .................... 558/36 |
| 5,928,654 A | * 7/1999 | Duranton | .................... 424/401 |
| 6,060,500 A | * 5/2000 | Bonewald et al. | .......... 514/418 |

OTHER PUBLICATIONS

Gene Map Locus: Chr. 10 *152390 Arachidonate 5–Lipoxygenase; Alox5.
Gene Map Locus: 7p.13.1 *152391 Arachidonate 12–Oxidoreductase; Alox12.
Gene Mao Locus: 17p13.3 *152392 Arachidonate 15–Lipoxygenase; Alox15.
Medline *603697 Arachidonate 15–Lipoxygenase, Second Type; Alox15B.
Gene Map Locus: 13q12 *603700 Arachidonate 5–Lipoxygenase–Activating Protein; Alox5AP.
Gene Map Locus: 17pter–p13.1 *603471 Arachidonate 12–Lipoxygenase, R Type; Alox12B.

* cited by examiner

*Primary Examiner*—Kevin E. Weddington
(74) *Attorney, Agent, or Firm*—Bret E. Field; Bozicevic, Field & Francis

(57) ABSTRACT

Allosteric inhibitors of lipoxygenase and methods for their use are provided. In many embodiments, the allosteric inhibitors are sulfated long chain alkenyl compounds. The compounds of these embodiments are long chain monounsaturated alkenyl compounds having a single sulfate moiety at the 1 position. In many embodiments, the subject compounds range in length from about 14 to 22 carbon atoms and the site of unsaturation is located between the 8 and 14 positions. Specific compounds of interest include 9-oleyl sulfate; 9-palmitoleyl sulfate and 11-eicosenyl sulfate. The subject compounds exhibit lipoxygenase inhibitory activity. As such, the subject compounds find use in treating disease conditions characterized by the presence of undesirable lipoxygenase activity. Also provided are pharmaceutical preparations of the subject compounds.

16 Claims, No Drawings

ALLOSTERIC INHIBITORS OF LIPOXYGENASE

INTRODUCTION

1. Field of the Invention

The field of this invention is lipoxygenase inhibitors.

2. Background of the Invention

Lipoxygenase are a structurally related family of non-heme iron deoxygenases that function in the production of fatty acid hydroperoxides. The lipoxygenases are present in a wide variety of organisms and catalyze the oxidation of unsaturated fatty acids utilizing an essential, non-heme iron atom. The generally accepted mechanism for lipoxygenases involves a hydrogen atom abstraction at C-3 of the 1,4-diene by Fe(III), with subsequent trapping of the pentadienyl radical by oxygen, forming the hydroperoxide product. In humans, the 5S-, 12S- and 15S-lipoxygenases oxygenate arachidonic acid in different positions along the carbon chain, e.g., as seen in leukotriene synthesis.

Lipoxygenase activity plays a critical role in asthma, atherosclerosis and cancer regulation, among other physiological processes and conditions. As such, the inhibition of lipoxygenase (LO) is currently an important goal of biomedical research. To date, a number of different types of lipoxygenase inhibitors have been identified.

However, there is continued interest in the identification of additional lipoxygenase inhibitors.

Relevant Literature

U.S. Patents of interest include: U.S. Pat. Nos. 4,645,627 and 5,037,992. Also of interest are: Lewis et al., J. Am. Chem. Soc. (1999) 121: 1395–1396; Sailer et al., Eur. J. Biochem. (1998) 256: 364–368; and Wang et al., Biochemistry (1993) 32: 1500–1509.

SUMMARY OF THE INVENTION

Allosteric inhibitors of lipoxygenase and methods for their use are provided. In many embodiments, the allosteric inhibitors are sulfated long chain alkenyl compounds. The compounds of these embodiments are long chain monounsatured alkenyl compounds having a single sulfate moiety at the 1 position. In many embodiments, the subject compounds range in length from about 14 to 22 carbon atoms and the site of unsaturation is located between the 8 and 14 positions. Specific compounds of interest include 9-oleyl sulfate; 9-palmitoleyl sulfate and 11-eicosenyl sulfate. The subject compounds exhibit lipoxygenase inhibitory activity. As such, the subject compounds find use in treating disease conditions characterized by the presence of undesirable lipoxygenase activity. Also provided are pharmaceutical preparations of the subject compounds.

DEFINITIONS

The term "lipoxygenase" is used to refer to a protein that catalyzes the oxidation of unsaturated fatty acids utilizing an essential, non-heme iron atom. Specific lipoxygenases of interest include, but are not limited to: soybean lipoxygenase-1; 15-human lipoxygenase; 12-human lipoxygenase; 5-human lipoxygenase; 9-human lipoxygenase; and the like.

The term "allosteric inhibitor" refers to a compound that inhibits lipoxygenase activity through binding to the allosteric binding site of the lipoxygenase protein.

"Alkenyl" means a linear monovalent hydrocarbon chain containing at least one double bond.

"Long chain" means a chain having a length of from about 14 to 22 carbon atoms in length.

"Monounsaturated" means a single site of unsaturation, e.g., a single double-bond between two carbon atoms in a compound.

DESCRIPTION OF THE SPECIFIC EMBODIMENTS

Allosteric lipoxygenase inhibitors and methods for their use in lipoxygenase inhibition are provided. In many embodiments of the subject invention, the inhibitors are sulfated long chain alkenyl compounds. The compounds of this embodiment are generally long chain monounsatured alkenyl compounds having a single sulfate moiety at the 1 position. In many embodiments, the subject compounds range in length from about 14 to 22 carbon atoms and the site of unsaturation is located between the 8 and 14 positions. Specific compounds of interest include 9-oleyl sulfate; 9-palmitoleyl sulfate and 11-eicosenyl sulfate. The subject compounds exhibit lipoxygenase inhibitory activity. As such, the subject compounds find use in treating disease conditions characterized by the presence of undesirable lipoxygenase activity. Also provided are pharmaceutical preparations of the subject compounds. In further describing the subject invention, the subject compounds will be described first in greater detail, followed by a review of methods for their use in the lipoxygenase inhibition.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Allosteric Lipoxygenase Inhibitors

As summarized above, the subject methods employ allosteric inhibitors of lipoxygenase. By allosteric inhibitor of lipoxygenase is meant a compound that binds to the allosteric binding site of lipoxygenase and at least slows, if not substantially stops, the lipoxygenase activity. As the subject compounds exhibit lipoxygenase inhibitory activity, in many embodiments the compounds exhibit a $K_1$ value of from about 0.05 to 1.5 $\mu$m, and usually from about 0.10 to 1.0 $\mu$m.

Allosteric lipoxygenase inhibitors employed in the subject invention are, in many embodiments, small molecule compounds. As the inhibitors of these embodiments are small molecules, they have a molecular weight that generally ranges from about 200 to 600, usually from about 250 to 500 and more usually from about 250 to 400 daltons.

In many embodiments of the subject invention, the allosteric lipoxygenase inhibitors employed in the subject methods are sulfated long chain alkenyl compounds. By sulfated long chain alkenyl compound is meant a long chain molecule of from about 14 to 22 carbon atoms in length, where in many embodiments the number of carbon atoms in the long chain of the compounds is between 16 and 20, e.g., 16, 18 or 20. The subject compounds of this embodiment exhibit good water solubility, where their solubility typically ranges from about 150 to 200 μm, usually from about 125 to 150 μm and more usually from about 75 to 100 μm. In addition, the subject compounds exhibit increased potency as compared to their carboxylic analogs (i.e., molecule which is the same as the subject molecule except that the sulfate moiety is replaced with a caboxylate moiety), where the magnitude of this increased potency typically ranges from about 30 to 50 fold.

As the subject compounds are alkenyl compounds, they include at least one site of unsaturation. In many embodiments, the at least one site of unsaturation is in the form of a carbon-carbon double bond. While there may be more than one site of unsaturation, in many embodiments, the compounds are monounsaturated alkenyl compounds, having a single site of unsaturation, e.g., a single carbon-carbon double bond. The site of monounsaturation typically lies between atoms 6 and 14, usually between atoms 7 and 13 and more usually between atoms 8 and 12 in the long chain alkenyl moieties of the compounds. Preferred sites of monounsaturation are positions 9 and 11 in many embodiments.

As summarized above, the subject compounds are sulfated compounds, by which is meant that they exhibit a sulfate moiety. The term "sulfate moiety" is used to refer not only to —$SO_3H$ but also ionized and salt forms thereof, e.g., —$SO_3$—; —$SO_3Na$; etc. In general, the subject compounds include a single sulfate moiety located at the terminal 1 position of the compounds.

In certain embodiments of the subject invention, the employed compound are described the formula:

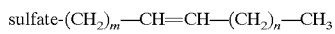

$$\text{sulfate-}(CH_2)_m\text{—}CH\text{=}CH\text{—}(CH_2)_n\text{—}CH_3$$

wherein:

m is an integer from 7 to 10; and n is an integer from 4 to 8.

Specific sulfated long chain alkenyl compounds of interest for use in the subject invention include, but are not limited to: 9-oleyl sulfate; 9-palmitoleyl sulfate; 11-eicosenyl sulfate; and the like.

The sulfated long chain alkenyl compounds employed in many embodiments of the subject invention may be fabricated using any convenient protocol. One representative protocol of interest is the protocol described in the Experimental Section, infra, in which a sulfate is added onto a fatty acid alcohol via a sulfamic acid/pyridine mixture. Another protocol that may be used to synthesize the subject sulfated long chain alkenyl compounds is disclosed in U.S. Pat. No. 5,037,992; the disclosure of which is herein incorporated by reference.

Methods of Lipoxygenase Inhibition

As summarized above, the subject invention provides methods of inhibiting lipoxygenase activity. By inhibiting lipoxygenase activity is meant at least a slowing, if not a substantial removal of, a protein's lipoxygenase activity, i.e., a protein's ability to catalyze the oxidation of unsaturated fatty acids. Where the methods result in a slowing the of the lipoxygenase activity, the degree of slowing is at least about 40 fold, usually at least about 45 fold.

In practicing the subject methods, a target lipoxygenase is contacted with an allosteric lipoxygenase inhibitor under conditions sufficient for lipoxygenase inhibition to occur. In the broadest sense, any compound that binds to the lipoxygenase allosteric binding site and consequently inhibits lipoxygenase activity may be employed. In many embodiments, the compound that is employed is a sulfated long chain alkenyl compound, as described above.

The mode of contact will vary depending on the environment of the target lipoxygenase. For example, where the target lipoxygenase is present in an in vitro environment, e.g., in a test tube, in a cell culture, etc., contact generally involves placing the allosteric inhibitor in the environment of the target lipoxygenase. Alternatively, where the target lipoxygenase is present in an in vivo environment, contact is generally achieved by administering an effective amount of the allosteric inhibitor to the host in which the in vivo environment is present. Administration may vary depending on the particular in vivo location, and may be systemic or local. A variety of different formulations and corresponding routes of administration are reviewed infra. By effective amount is meant an amount effective to cause the desired amount of lipoxygenase inhibition. The amount administered to a host may vary significantly depending on the nature of the compound, the nature of the host, the location of the target lipoxygenase, the route of administration, etc., where the dosages may readily be determined empirically by those of skill in the art.

The subject methods of inhibiting lipoxygenase activity find use in a variety of different applications, including the treatment of a variety of different disease conditions associated with lipoxygenase activity in a variety of different hosts. Representative conditions in which the subject methods find use include, but are not limited to: the treatment of asthma, atherosclerosis, cellular proliferative diseases, e.g., cancer, psoriasis, etc., inflammation, bone resorption suppression, removal of hair (See U.S. Pat. No. 5,928,654, dislosure of which is herein incorporated by reference), and the like.

By treatment is meant at least an amelioration in the symptoms of the disease conditions experienced by the host, where treatment can include substantially complete cessation, if not complete cessation of symptoms and/or substantially complete removal, if not complete removal of the underlying cause of the symptoms.

As mentioned above, the compounds of the subject invention find use in treating conditions in a variety of different hosts. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Pharmaceutical Preparations

Also provided are pharmaceutical preparations of the subject allosteric lipoxygenase inhibitor compounds. The subject compounds can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Kits with unit doses of the compounds, usually in oral, injectable or topical doses, are provided. In such kits, in addition to the containers containing the unit doses will be an informational package insert describing the use and attendant benefits of the drugs in treating pathological condition of interest. Preferred compounds and unit doses are those described herein above.

The following examples are offered by way of illustration and not by way of limitation.

EXPERIMENTAL
I. MATERIALS AND METHODS

Materials. SLO-1 and 15-HLO were expressed and purified as described previously. Holman et al., J. Am. Chem. Soc. (1998) 120: 12564–12572. Iron content of SLO-1 and 15-HLO were determined on a Finnegan inductively coupled plasma mass spectrometer (ICP-MS), using standardized iron solutions. All kinetic measurements were standardized to iron content.

Fatty Acid Synthesis. OS ($C_{18}H_{36}O_4S$) (oleyl sulfate or (Z)-9-octadecenyl sulfate) and linoleyl sulfate (LS) ($C_{18}H_{34}O_4S$) were prepared by a similar procedure to that of Axelrod and coworkers. Bild et al., Lipids (1977) 12:732–735. One gram of the fatty acid was dissolved under nitrogen in 3.6 mL of 1 M $LiAlH_4$ (dry THF). The mixture was refluxed for 2 hours and quenched with saturated $NH_4Cl$. The solution was filtered, dried over $Na_2SO_4$ and evaporated to dryness. The resulting oil was dissolved in 6 mL of dry pyridine and 0.5 grams of sulfamic acid were added. The reaction was heated at 95° C. for 1.5 hours under nitrogen and stopped with the addition of 20 mL of methanol and 1 mL of saturated $Na_2CO_3$. The waste solids were filtered off and the solution was evaporated to dryness. The resulting residue was re-crystallized from hot methanol and the white solid gave a single spot by TLC (silica gel), developed in hexane:ether:acetic acid (60:39:1). The $^1H$ NMR signals ($CDCl_3$) for OS were observed at δ5.35 (br m, 2H), 4.02 (t, 2H), 2.01 (br m, 4H), 1.65 (br m, 2H), 1.30 (br m, 22H), 0.89 (t, 3H). The $^1H$ NMR signals ($CDCl_3$)for LS were observed at δ5.35 (br m, 4H), 4.02 (t, 2H), 2.77 (t, 2H), 2.05 (q, 4H), 1.66 (br m, 2H), 1.33 (br m, 16H), 0.90 (t, 3H).

Fatty Acid Purification. LA (Linoleic Acid) was purchased from Aldrich Chemical Co. and per-deuterated linoleic acid (D-LA) was purified from a mixture of per-deuterated algal fatty acids from Cambridge Isotope labs. The algal fatty acid mixture was esterified, loaded onto a 10% Ag-silica column (800 grams of silica), washed with hexane and eluted with ethyl acetate:hexane (2:98). The fractions were analyzed by electron ionization mass spectroscopy (EI-MS) and those containing D-LA were combined, evaporated to dryness and de-esterified overnight, with an ethanol:2.5 M NaOH (aq.) mixture (50:50). The sample was then extracted with $CH_2Cl_2$ and evaporated to dryness. The D-LA was depleted of mono-protonated substrate with SLO-1, exhaustively extracted with $CH_2Cl_2$ and purified twice by a Waters 625 HPLC with a C18 column (Higgins Analytical, 5 micron, 250×10 mm, isocratic mobile phase: 86.9% Methanol: 13% $H_2O$ : 0.1% Acetic acid at 3 ml/min). Substrate was detected by on-line UV absorption (210 nm) and had a retention time of approximately 30 minutes. Substrate fractions were collected, evaporated to dryness, re-dissolved in ethanol and stored at −20° C. The LA was also purified by RP-HPLC and combined with the D-LA to the appropriate ratio. The LA/D-LA ratio was verified by complete conversion to the products with SLO-1 and the LA and D-LA products separated by HPLC (vide infra). A negative control is performed to ensure that auto-oxidized substrate is not present in the substrate mixture. This is critical because impurities can dramatically affect the KIE values. The concentration of substrate was determined by enzymatically converting 1 mL of diluted LA stock to product. The product absorbs at 234 nm with an extinction coefficient of 25,000 $M^{-1}cm^{-1}$. All other reagents were of analytical grade or higher.

OS Quantitation. OS was solubilized directly in water and its concentration determined by EI-MS and NMR using an internal standard of LS. LS concentrations were determined by using soybean lipoxygenase-1 to convert 100% of the LS to the hydroperoxide product ($\epsilon$=25,000 $M^{-1}cm^{-1}$, assuming a similar $\epsilon$ to 13-HPOD). Aqueous OS solutions containing fixed amounts of LS were injected via syringe pump with a continuous flow at 0.01 ml/min. Mass spectral data were obtained when the m/z signal of both compounds had stabilized and after voltage was optimized. Intensities of both compounds were averaged over several scans and concentrations determined using relative ratios. A NMR spectra ($CDCl_3$) was taken of a similar mixture of OS and LS and their relative ratios determined by comparing their signal integrations. Both methods were in agreement within 15%. It should be noted that OS tends to stick to various materials which lowers its apparent concentration and care should be taken when aliquoting solutions.

Surface Tension Measurements. Buffers were used which correspond to those of the kinetic measurements. Surface tension was measured as described by Harkins et al., using a thin platinum plate (perimeter 2.5 cm) and a Cahn electro-microbalance. Harkins et al., J. Am. Chem. Soc. (1937) 59:2189–2197. Various amounts of surface active agent were added to a 30 ml buffer solution and the surface tension was continuously recorded. After each addition, a sufficiently long period of time (10–30 min.) was allowed to elapse before attaining a steady value of the surface tension. Critical micelle concentration (CMC) values were obtained by plotting the measured surface tensions versus the logarithm of the concentrations of the surface-active agent and recording the intercept of the two straight lines. The point at which a deviation from the straight line, as observed in the surface tension versus log [surface-active agent] plot, was defined as the start of pre-micellular aggregate formation. Harkins et al., supra; Verhagen et al., Chem. Phys. Lipids (1978) 22:255–259.

Kinetic Isotope Effect Determination. Determination of the kinetic isotope effect (KIE) was similar to that previously published by Holman and coworkers with the following modifications. Lewis et al., J. Am. Chem. Soc. (1994) 116:795–796. Lipoxygenase is added (0.12 nM SLO-1 and 12 nM 15-HLO) to a protio/per-deutero LA mixture (60 mL, 5 $\mu$M LA/D-LA), monitored at 234 nm with a P-E Lambda 4 and stopped with an acid quench (5% glacial acetic acid) at less than 5% total LA/D-LA consumption. It is important to note that diode array spectrophotometers degrade 13-hydroperoxy-9,11-(Z,E)-octadecadienoic acid (13-HPOD) and care should be taken if the reaction time length is longer than 5 minutes. The acidified reaction mixture is extracted with methylene chloride (trimethylphosphite, which quantitatively reduces the labile 13-HPOD, is not needed since both the alcohol and the peroxide have the same elution time). The methylene chloride layer is evaporated to dryness under vacuum, reconstituted in 50 $\mu$L running buffer, injected onto a C18 column (Higgins Analytical, 5 micron, 250×4.6 mm), and eluted at 1 mL/min. (isocratic mobile phase: 74.9% Methanol :25% $H_2O$: 0.1% Acetic acid). As described previously by our lab, RP-HPLC separates the per-deutero 13-HPOD from the protio 13-HPOD with baseline separation and retention times of approximately 20 and 22 min., respectively. Lewis et al., supra. The molar protio/per-deutero 13-HPOD ratios are equated to the corresponding peak area ratios and the competitive KIE ($^P[k_{cat}/K_m]$) is then calculated from $(\ln(1-f))/(\ln((1-(f*R_p/R_o)))$, where $R_o$ is the mass ratio of the starting substrate and $R_p$ is the mass ratio of the product at the extent of reaction (f). When the percent conversion (f) to product is less than 5%, this equation simplifies to ([P-H]/[P-D]])*([$S_o$-D]/[$S_o$-H]), where [P-H] is protio-product concentration and [$S_o$-H] is the initial protio-substrate concentration. Melander et al., Reaction Rates of Isotopic Molecules (R. E. Krieger Publishing, Florida)(1987). Both equations gave comparable results within experimental error. The typical ratio of per-deutero to protio substrate is approximately 2:1, respectively. Greater substrate ratios than 2:1 were not used due to the expensive nature of the per-deutero substrate. Under these conditions, the upper limit for the KIE is greater than 130 and is limited by the vanishingly small peak area of the per-deutero 13-HPOD peak relative to the negative control. This RP-HPLC based method for determining molar protio/per-deutero 13-HPOD ratios gave results identical (within experimental error) to those obtained by EI-MS. No appreciable side products at any wavelength for 15-HLO or SLO-1 were observed, indicating no reaction branching. The OS titration experiments require 5 $\mu$M LA/D-LA to record product ratios. For the 15-HLO experiments (pH 7.5), OS concentrations above 6 $\mu$M were not feasible due to large amounts of a white emulsion at the extraction interface which inhibited product recovery. This emulsion was not observed for reactions performed with SLO-1 (pH 9.2). It is believed that the emulsion may be due to a precipitated protein/fatty acid aggregate because the 15-HLO reaction has over 100-fold more enzyme and not due to a pH difference since both extractions contain excess acetic acid. All kinetic data reported were measured in triplicate on two distinct days.

Steady State Kinetics. Lipoxygenase rates were determined by following the formation of product at 234 nm ($\epsilon$=25,000 $M^{-1}cm^{-1}$) with a Hewlett-Packard 8453 UV-vis spectrophotometer. The destruction of 13-HPOD by the diode array spectrophotometer were negligible under these reaction conditions. All reactions were 2 ml in volume, run at room temperature (23° C.) and constantly stirred with a rotating magnetic bar. In experiments using SLO-1, kinetic reactions were performed in 0.1 M borate (pH 9.2), while reactions using 15-HLO were performed in 25 mM HEPES (pH 7.5). Substrate solutions used in each experiment were measured for accurate LA concentration by quantitatively converting substrate to product using soybean lipoxygenase-1. Enzymatic rates were measured between 1–50 $\mu$M LA with 1–25 $\mu$M OS for SLO-1 and lower than 2 $\mu$M LA for 15-HLO. Solutions containing LA and/or OS were sonicated for 3–5 minutes before use in kinetic experiments. Rate reactions were initiated by the addition of enzyme to final concentrations of 3 nM SLO-1 (80% iron content) and 200 nM 15-HLO (15% iron content). All kinetic parameters were determined by non-linear regression using Kaleidagraph software (Abelbeck).

Viscosity. Buffer and substrate solutions of 0 and 30% by weight glucose, in 0.1 M CHES buffer, pH 9.2, 20° C., were prepared corresponding to relative viscosities ($\eta_{rel}$) of 1 and 3, respectively ($\eta_{rel}$ =$\eta/\eta°$, $\eta°$ is the viscosity of $H_2O$ at 20 C, CRC Handbook of Chemistry). Sucrose and ethylene glycol were not used as viscogenic agents due to inhibition and borate reacts with glucose to lower its buffering capacity. Glickman et al., Biochemistry (1995) 34:14077–14092.

II. RESULTS

Surface Tension Measurements: CMC values have been determined for LA in 0.1 M borate (pH 9.2) and 25 mM HEPES (pH 7.5) to be 150±10 and 40±10 $\mu$M, respectively (data not shown). These values correlate well with those of the literature and indicate the dramatic loss in solubility of LA as pH decreases. Verhagen et al., Chem. Phys. Lipids (1978) 22:255–259. Addition of 16 $\mu$M OS has no significant effect on the CMC of LA at pH 9.2. However, at pH 7.5, addition of 5 and 10 $\mu$M OS results in a deviation from linear behavior at approximately 25±5 $\mu$M total fatty acid (FA) concentration (LA and OS). This indicates the formation of mixed pre-micellular aggregates of LA and OS, possibly due to hydrogen bond interactions between the protonated LA and the de-protonated OS.(21) These aggregates could conceivably be enzymatic substrates and for this reason only kinetic data below 20 $\mu$M total FA (pH 7.5) are used in the current study for 15-HLO.

Kinetic Isotope Effect. Previously, it has been shown that oleic acid (OA) increases the KIE of SLO-1. Lewis et al., supra. Titration of increasing amounts of OA, into a constant LA/D-LA mixture of 5 $\mu$M, reveals a hyperbolic rise in the KIE which suggests the formation of a catalytically active ternary complex. The data can be fit to a simple saturation curve yielding a $K_D$ of 36±14 $\mu$M OA. This value is within experimental error of the accepted $K_i$ for OA ($K_i$ 22 $\mu$M) (Vanderheijdt et al., Eur. J. Biochem. (1992) 207:793–802) which supports a direct correlation between OA inhibition and the rise in KIE. In order to investigate this effect further, a series of KIE experiments were performed for both SLO-1 and 15-HLO with OS, a more soluble analogue of OA, that has never before been used as a lipoxygenase inhibitor. The KIE of SLO-1 was observed to sharply rise as OS is added. A hyperbolic fit to the change in KIE ($\Delta$KIE) yields a $K_D$ value of 0.6±0.2 $\mu$M, which represents an approximate 60-fold increase in binding affinity over that of OA. The KIE for 15-HLO also manifests a hyperbolic increase as OS is added, yielding a $K_D$ value of 0.4±0.05 $\mu$M. The increase in KIE for both SLO-1 and 15-HLO can best be explained by a decrease in commitment ($k_2/k_{-1}$). The kinetic mechanism for SLO-1 can be minimally described by Scheme 1, where $k_2$ is the RDS and $k_{-2}$ is 0 ($k_2$ is approximately 5000-fold greater than $k_{-2}$).

Scheme 1

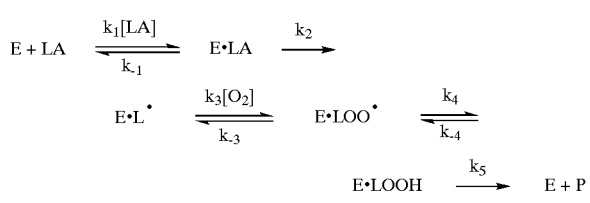

This was previously determined by Klinman and coworkers and is considered an accurate description of the SLO-1 reaction for this study. Glickman et al., Biochemistry (1996) 35:12882–12892. According to Scheme 1, the KIE is described by the following equation, $$\text{KIE} = {}^D[k_{cat}/K_m] = (k_{cat}/K_m)^H/(k_{cat}/K_m)D = (k_2^H/k_2^D + k_2^H/k_{-1}^H)/(1 + k_2^H/k_{-1}^H) \quad \text{(Eq. 1)}$$

where substrate release ($k_{-1}$) and C—H bond cleavage ($k_2$) are the primary determinants for the KIE (This assumes $k_2 = k_{cat}$). The KIE increases to a maximum of $k_2^H/k_2^D$ when commitment ($k_2^H/k_{-1}^H$) is small and decreases, approaching 1, when commitment is large. This assumes that the intrinsic $k_2^H/k_2^D$ remains unchanged. Control experiments using SDS revealed no increase in the KIE and thus eliminates the possibility of non-specific surfactant binding as a cause for the increase in KIE.

Inhibition Studies. The steady-state kinetic parameters were determined for both SLO-1 and 15-HLO with increasing amounts of OS. SLO-1 exhibits a striking hyperbolic response to increasing amounts of OS with an increase in $K_m$ apparent (app) from 12.5 $\mu$M to a saturating value of 50 $\mu$M. The. $k_{cat}/K_m$ (s$^{-1}\mu$M$^{-1}$) decreases from 19 to 5 s$^{-1}\mu$M$^{-1}$ while $k_{cat}$ decreases from 237 to 180 s$^{-1}$. The saturation behavior of the $K_m$ (app) and $k_{cat}/K_m$ is indicative of hyperbolic inhibition (i.e. partial inhibition) which suggests the presence of an allosteric binding site that affects catalysis by changing the microscopic rate constants of the enzyme, Scheme 2.

Scheme 2

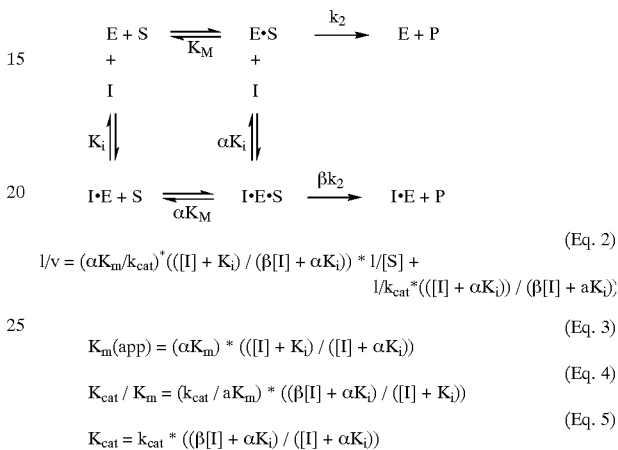

$$1/v = (\alpha K_m/k_{cat})^* (([I] + K_i) / (\beta[I] + \alpha K_i)) * 1/[S] + 1/k_{cat}^*(([I] + \alpha K_i)) / (\beta[I] + aK_i)) \quad \text{(Eq. 2)}$$

$$K_m(\text{app}) = (\alpha K_m) * (([I] + K_i) / ([I] + \alpha K_i)) \quad \text{(Eq. 3)}$$

$$K_{cat} / K_m = (k_{cat} / aK_m) * ((\beta[I] + \alpha K_i) / ([I] + K_i)) \quad \text{(Eq. 4)}$$

$$K_{cat} = k_{cat} * ((\beta[I] + \alpha K_i) / ([I] + \alpha K_i)) \quad \text{(Eq. 5)}$$

From Scheme 2, equations 2–5 are derived which allow for the determination of three parameters; the strength of inhibitor binding ($K_i$), the change in $K_m$ ($\alpha$) and the change in $k_{cat}$ ($\beta$). A fit to the $K_m$ (app) saturation curve with Eq. 3 ($k_{cat}$=237 s$^{-1}$, $K_m$=12.4 $\mu$M), yields an $\alpha$ of 4.0±0.3 and a $K_i$ of 0.45±0.16 $\mu$M, indicating an increase in $K_m$ (app) by a factor of 4. These values of $\alpha$ and $K_i$ can be entered into Eq. 4 and fit to the $k_{cat}/K_m$ data, which results in a $\beta$ of 0.9±0.1. A more precise method of determining $\beta$ is from the $k_{cat}$ data, however, the data are not accurate enough to fit directly. This is possibly due to the extended lag phase induced by high concentration of OS which could hinder an accurate determination of $k_{cat}$. Mathematical simulations were therefore used to determine an approximate value for $\beta$. If the following kinetic values are entered into Eq. 5 ($k_{cat}$=237 s$^{-1}$, $K_m$=12.4 $\mu$M, $\alpha$=4.0 and $K_i$=0.45 $\mu$M) and the value for $\beta$ varied ($\beta$=0, 0.9, 0.85, 0.75), an approximate maximal and minimal value for $\beta$ can be determined. The mathematical simulations indicate that $\beta$ is less than 0.9 but greater than 0.75. If we approximate $\beta$ to be 0.85, according to the best fit to the $k_{cat}$ data, and repeat the fit to the $k_{cat}/K_m$ data (Eq. 4), this yields values for $\alpha$ and $K_i$ of 5.2±0.6 and 0.86±0.11, respectively. The average values for $\alpha$ and $K_1$ derived from the $K_m$ (app) and $k_{cat}/K_m$ data, are 4.6±0.5 and 0.7±0.3, respectively and $\beta$ is approximated to be 0.85±0.1. These values define the kinetics as mixed hyperbolic inhibition ($\alpha$>1 and $\beta$<1), yet it is clear that that the major kinetic change is in the value of $K_m$ ($\alpha$=4.6±0.5), with only a slight shift in $k_{cat}$ ($\beta$=0.85±10.1). The hyperbolic inhibition data thus indicate the formation of a catalytically active ternary complex, (inhibitor-enzyme-substrate, I•E•S) and strongly suggests the presence of an allosteric site in SLO-1.

The data can also be modeled with OS binding to both the allosteric and catalytic sites (Scheme 3, Eqs. 6–9), however the fit to the $K_m$ data with Eq. 7 yields negative values for $\delta$ and $K_{ii}$, which indicate a poor model.

Scheme 2

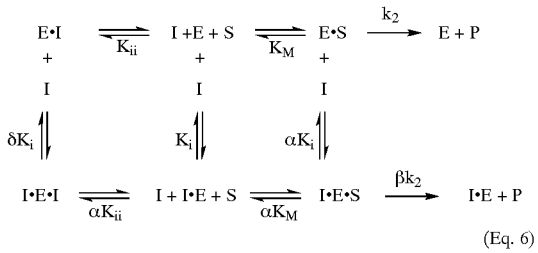

$$1/v = K_m/k_{cat}* ((1 = [I](L/K_i + 1/K_{ii}) + [I]^2(1/\delta K_i K_{ii})) / ((1 + [I](\beta/\alpha K_i)) * 1/S + 1/k_{cat}*(1 + [I](1/\alpha K_i)) / (1 + [I](\beta/\alpha K_i)) \quad (Eq. 7)$$

$$K_m(app) = K_m * ((1 + [I](1/K_i + 1/K_{ii}) + [I]^2(1/\beta K_i K_{ii})) / (1 + [I](1/\alpha K_i)) \quad (Eq. 8)$$

$$k_{cat}/K_m = k_{cat}/K_m * (1 + [I](\beta/aK_i)) / ((1 + [I](1/K_i + 1/K_{ii}) + [I]^2(1/\beta K_i K_{ii})) \quad (Eq. 9)$$

$$k_{cat} = k_{cat} * (1 + [I](\beta/aK_i)) / (1 + [I](1/\alpha K_i))$$

If we attempt to mathematically simulate the $K_m$ (app) and $k_{cat}/K_m$ data with Eqs. 7 and 8, respectively, ($k_{cat}$=237 s$^{-1}$, $K_m$=12.4 μM, α=4.6 and $K_i$=0.7 μM) and vary δ and $K_{ii}$, we observe poor correlation with the data. The best simulation of the data requires a minimal value of $K_{ii}$ to be over 140-fold (100 μM) higher than that of OS for the allosteric site and a δ of 4, comparable to α. The data can also be fit if the value of $K_{ii}$ is lowered, however, the δ value increases to an unreasonably high value ($K_{ii}$=20 μM, δ=10). Therefore, these simulations demonstrate that OS weakly binds to the catalytic site and does not appreciably affect the kinetic rates. This is qualitatively demonstrated by the lack of a large increase in K-$_M$ (app) at high OS concentration. The $k_{cat}/K_m$ data can also be simulated to Scheme 3, however, it is relatively insensitive to δ and $K_{ii}$, as seen by the lack of variation of the simulation curves. The $k_{cat}$ data were not simulated because Eq. 9 does not include 67 or $K_{ii}$ terms. The substrate was not modeled as binding to the allosteric site since we do not observe appreciable substrate inhibition below 30 μM LA, as demonstrated in previous studies. Wang et al., Biochemistry (1993) 32:1500–1509.

OS also induces a decrease in the $k_{cat}/K_m$ for 15-HLO, however, due to pre-micellular aggregation of LA and OS at pH 7.5, only data below 20 μM total FA could be used for analysis. This reduces the available range of LA and OS concentrations and introduces a high degree of error in the mathematical fits, thus limiting any use of the steady state $K_m$ (app) and $k_{cat}$ values. Consequently, we have utilized the $k_{cat}/K_m$ values derived from the initial slope of the velocity curves, where substrate concentration is low ([LA]<<$K_m$), and we observe that $k_{cat}/K_m$ manifests a hyperbolic decrease which can not be explained by simple competitive inhibition. The decrease in $k_{cat}/K_m$ saturates at H 16 μM OS and is similar to the saturation behavior of its KIE. Unfortunately, α and β can not be determined with only the $k_{cat}/K_m$ data, however, the response of $k_{cat}/K_m$ to addition of OS is consistent with hyperbolic inhibition.

Viscosity Measurements. Lipoxygenase is a fast enzyme that is 50% diffusion limited ($k_{cat}/K_m$ 3×10$^7$ M$^{-1}$s$^{-1}$ at 20° C.). Glickman et al., supra. Viscosity dependence experiments were performed on SLO-1 at 10 μM OS (η/η°=1 & 3) and clearly indicate that addition of OS abolishes all effect of viscosity on the specific activity. The $k_{cat}/K_m°/k_{cat}/K_m$ is 1.4±0.1 with no OS present and 1.0±0.1 with 10 μM OS, where $k_{cat}/K_m°$ has a η/η° of 1 and $k_{cat}/K_m$ has a η/η° of 3. This result can be explained by a decrease in commitment upon addition of OS. If we assume lipoxygenase proceeds through the previously determined reaction sequence (Glickman et al., supra) (i.e. Scheme 1, $k_2$ is the RDS and $k_{-2}$ 0), then the kinetic equations may be simplified and defined as $$k_{cat}/K_m=(k_1°(k_2/k_{-1}°)*(η°/η))/((k_2/k_{-1}°)+(η°/η)) \quad (Eq.6)$$

where the relative viscosity ($η_{rel}$=η/η°) is the viscosity of solution compared to aqueous solution at 20° C. and commitment is defined as $k_2/k_{-1}$. This equation dictates that as commitment decreases in magnitude, the effect of viscosity on $k_{cat}/K_m$ also decreases to a limit of $k_{cat}/K_m°(η/η°=1)/k_{cat}/K_m(η/η°=3)$=1. This limit is achieved after addition of 10 μM OS and indicates that OS binding decreases commitment for SLO-1. This treatment is general and based solely on two assumptions: (1) Each and every microscopic bimolecular association and dissociation is diffusion-controlled and (2) The rate of a microscopic diffusion-controlled step is inversely proportional to the viscosity of the medium as dictated by the Stokes-Einstein equation. Brouwer et al., Biochemistry (1992) 31:7700–7706.

III. DISCUSSION

The above described independent experimental results (increase in KIE, hyperbolic inhibition, and loss of diffusion dependence) all indicate a decrease in commitment and are best explained by the presence of an allosteric site on the lipoxygenase enzyme. The lowered commitment ($k_2/k_{-1}$) is possibly achieved by an OS-induced conformational change in SLO-1 which lowers the affinity for substrate by a factor of 4.6 (i.e. $k_{-1}$ (off-rate) increases, α=4.6±0.5) and lessens the rate of catalysis by 15% (i.e. $k_2$ decreases, β=0.85). It is clear that the increased off rate ($k_{-1}$) is the dominate factor in the kinetic rate change and hence has the more pronounced effect on the enzymatic inhibition. This inhibitor-based conformational change is supported by trypsin digest studies of SLO-1 which reveal differences in proteolysis patterns upon binding of OA. Ramachandran et al., Biochemistry (1992) 31:7700–7706 and Ramachandran et al., Biochemistry (1995) 344: 14868–14873. It should be noted that our model can not distinguish between two molecules binding within the catalytic site (i.e. one OS and one LA) or OS binding to a completely separate binding site. We are currently performing further studies to locate the allosteric site and characterize the molecular determinants of OS binding.

The above results indicate that 15-HLO (15 human lipoxygenase) also displays kinetic properties consistent with the presence of an allosteric site. The KIE increases with addition of OS ($K_D$ of 0.4±0.05 μM) and the steady state kinetics ($k_{cat}/K_m$) saturate at H16 μM OS, both indicative of a decrease in commitment, as seen for SLO-1 in this paper. Although α and β can not be determined due to FA aggregation, the qualitative hyperbolic response of the KIE and the $k_{cat}/K_m$ for 15-HLO upon addition of OS, strongly suggest the presence of an allosteric site. Further studies are currently in progress to fully characterize this allosteric site in 15-HLO and determine its inhibition parameters (i.e. α and β).

In conclusion, the current data indicate that OS is a potent lipoxygenase inhibitor that tightly binds to an allosteric site for both SLO-1 and 15-HLO ($K_D$=0.6±0.2 and $K_D$=0.45±0.05, respectively). The sulfate moiety of OS increases the affinity 60-fold over that of the corresponding carboxylic acid in OA for SLO-1 and contributes to the selectivity of OS binding to the allosteric site (OS, $K_D$=0.6

μM; OA, $K_D$ 36 μM; LA, $K_D$>30 μM). This is significant regarding the inhibition of lipoxygenase since it indicates the allosteric site as a new chemical target against asthma, atherosclerosis and cancer.

It is apparent from the above results and discussion that the subject invention provides an important new way to inhibit lipoxygenase activity. The subject methods find use in a variety of different applications, including the treatment of a variety of different disease conditions. Accordingly, the subject invention is an important contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of inhibiting lipoxygenase activity, said method comprising:
   contacting said lipoxygenase with a lipoxygenase allosteric antagonist, wherein said lipoxygenase allosteric antagonist is a sulfated long chain alkenyl compound.

2. The method according to claim 1, wherein said compound comprises a monounsaturated alkenyl moiety.

3. The method according to claim 2, wherein said monounsaturated alkenyl moiety is from 14 to 22 carbon atoms in length.

4. The method according to claim 2, wherein said site of unsaturation lies between positions 8 and 14 of said compound.

5. The method according to claim 1, wherein said sulfated long chain alkenyl compound comprises a single sulfate moiety at the 1 position.

6. A method of inhibiting lipoxygenase activity, said method comprising:
   contacting said lipoxygenase with a sulfated long chain monounsaturated alkenyl compound of from 14 to 22 carbon atoms in length and having a single sulfate moiety at the 1 position.

7. The method according to claim 6, wherein said site of unsaturation lies between positions 8 and 14 of said compound.

8. The method according to claim 6, wherein said compound is described the formula:

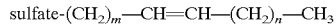

wherein:
   m is an integer from 7 to 10; and
   n is an integer from 4 to 8.

9. The method according to claim 8, wherein said compound is selected from the group consisting of 9-oleyl sulfate; 9-palmitoleyl sulfate and 11-eicosenyl sulfate.

10. The method according to claim 6, wherein said lipoxygenase is selected from the group consisting of: human 15 lipoxygenase, human 12 lipoxygenase and soybean lipoxygenase 1.

11. A method of treating a host for a disease condition treatable through administration of a lipoxygenase inhibitor, said method comprising:
   administering to said host an effective amount of a lipoxygenase allosteric antagonist, wherein said lipoxygenase allosteric antagonist is a sulfated long chain alkenyl compound.

12. The method according to claim 4, wherein said sulfated long chain alkenyl compound comprises a monounsaturated alkenyl moiety of from 14 to 22 carbon atoms in length.

13. The method according to claim 12, wherein said site of unsaturation lies between positions 8 and 14 of said compound.

14. A pharmaceutical preparation comprising a lipoxygenase allosteric antagonist and a pharmaceutically acceptable carrier, wherein said lipoxygenase allosteric antagonist is a sulfated long chain alkenyl compound.

15. The preparation according to claim 14, wherein said compound comprises a monounsaturated alkenyl moiety of from 14 to 22 carbon atoms in length.

16. The preparation according to claim 15, wherein said site of unsaturation lies between positions 8 and 14 of said compound.

* * * * *